United States Patent [19]

Henkelmann et al.

[11] Patent Number: 5,136,089
[45] Date of Patent: Aug. 4, 1992

[54] ACYLATION OF ALKYL AROMATIC HYDROCARBONS

[75] Inventors: Jochem Henkelmann, Ludwigshafen; Hardo Siegel, Speyer, both of Fed. Rep. of Germany

[73] Assignee: BASF Aktiengesellschaft, Ludwigshafen, Fed. Rep. of Germany

[21] Appl. No.: 681,890

[22] Filed: Apr. 8, 1991

[30] Foreign Application Priority Data

Apr. 12, 1990 [DE] Fed. Rep. of Germany ....... 4011916

[51] Int. Cl.$^5$ .............................................. C07C 59/76
[52] U.S. Cl. ...................................................... 562/460
[58] Field of Search ........................................ 562/460

[56] References Cited

U.S. PATENT DOCUMENTS

| | | | |
|---|---|---|---|
| 4,895,984 | 1/1990 | Eggersdorfer et al. | 568/319 |
| 4,952,714 | 8/1990 | Welborn, Jr. | 556/179 |
| 4,968,653 | 11/1990 | Meverden et al. | 502/116 |

FOREIGN PATENT DOCUMENTS 0248423 of 1987 European Pat. Off. .
173105 7/1990 Japan .

OTHER PUBLICATIONS

C. A. Olah, Friedel-Crafts and Related Reactions, vol. 1, p. 207 and vol. 3, Part I, pp. 550 et seq., Interscience (1964).
Houben-Weyl, "Methoden der Organischen Chemie", vol. XIII/4, pp. 78-80 (1970).

*Primary Examiner*—Paul J. Killos
*Attorney, Agent, or Firm*—John H. Shurtleff

[57] ABSTRACT

A process for the acylation of an alkyl aromatic hydrocarbon with a derivative of carboxylic acid by the Friedel-Crafts method in the presence of a Friedel-Crafts catalyst and an organo-aluminum compound, wherein the organo-aluminum compound is an alumoxane.

11 Claims, No Drawings

ACYLATION OF ALKYL AROMATIC HYDROCARBONS

The present invention relates to an improved process for the acylation of an alkyl aromatic hydrocarbon with a derivative of carboxylic acid by the Friedel-Crafts method in the presence of a Friedel-Crafts catalyst and an organo-aluminum compound.

The Friedel-Crafts acylation of aromatic hydrocarbons with carboxylic acid derivatives is generally known, but the problems arising in the acylation of alkyl aromatic hydrocarbons have not found an entirely satisfactory solution. When conventional Friedel-Crafts catalysts such as aluminum halides are used, hydrogen halide is liberated which encourages the formation of resinous by-products and the cleavage and isomerization of alkyl groups (C. A. Olah Friedel-Crafts and Related Reactions, Vol. 1, p. 207 and Vol. 3, Part I, pp. 550 et seq., Interscience 1964). The inclusion of a metal alkyl or metal alkyl halide in the system has proved to be effective in removing the hydrogen halide (EP-A 0,248,423), but such compounds are themselves active as catalysts for the isomerization of alkyl aromatic hydrocarbons.

It is an object of the present invention to suppress these side-reactions more effectively than hitherto.

Accordingly, we have found a process for the acylation of an alkyl aromatic hydrocarbon with a derivative of carboxylic acid by the Friedel-Crafts method in the presence of a Friedel-Crafts catalyst and an organo-aluminum compound, wherein the organo-aluminum compound is an alumoxane.

Particularly suitable alumoxanes are compounds of the general formula I

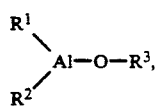

in which

R$^1$ denotes an alkyl group of from 1 to 12, preferably from 1 to 6 and more preferably from 1 to 4, carbon atoms, such as n-propyl, iso-propyl, and especially methyl, ethyl, and n-butyl.

R$^2$ denotes an alkyl or alkoxy group of from 1 to 12, preferably from 1 to 6 and more preferably from 1 to 4, carbon atoms, such as any one of the radicals denoted by R$^1$ or a propoxy or, in particular, a methoxy, ethoxy, or butoxy group, and R$^3$ has the meaning stated for R$^1$ or denotes a radical of the formula Ia

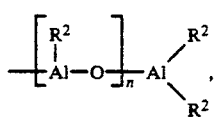

in which n stands for a mean value ranging from 0 to 50, in particular from 15 to 40.

The alumoxanes which are characterized by the radical Ia are by definition linear compounds. Such alumoxanes can be obtained, for example, by the processes described in Houben-Weyl, "Methoden der Organischen Chemie", Vol. XIII/4, pp 78–80, Thieme, Stuttgart, 1970, and in U.S. Pat. No. 4,952,714.

Other suitable compounds are cyclic compounds having a similar structure of the formula Ib

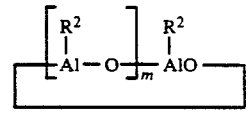

in which m is a mean value ranging from 3 to 12. The linear and cyclic alumoxanes can be manufactured by careful hydrolysis of aluminum alkyl compounds (Houben-Weyl, "Methoden der Organischen Chemie", Vol. XIII/4, pp. 76–78, 1970).

The effect achieved by the alumoxane results from the fact that any hydrogen halide present before or formed during the Friedel-Crafts reaction is eliminated by reaction of the alkyl-Al groups therewith to form hydrocarbon and aluminum halide as follows:

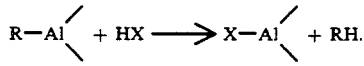

Thus the theoretically required amount of compound I is equal to the molar amount of alkyl-aluminum bonds, which is in turn equimolar to the eliminated hydrogen halide. However, since a portion of the hydrogen halide immediately escapes from the reaction mixture, smaller quantities of compound I are frequently sufficient. Normally, the amount of compound I will be equivalent to from 0.1 to 1.1 moles of alkyl-aluminum bonds per mole of carboxylic derivative.

Since the resulting compounds

themselves act as Friedel-Crafts catalysts, there is correspondingly less need for initial catalyst, eg AlCl$_3$. Generally speaking, only 60–90% of initial catalyst is required as compared with the amount which would be needed if no compound I were used for acylation.

It is equally possible to use larger amounts of Friedel-Crafts catalyst.

Suitable Friedel-Crafts catalysts are those compounds which are conventionally used in this reaction, for example FeCl$_3$, ZnCl$_2$, and TiCl$_4$, but preferably aluminum halides such as, in particular, aluminum bromide and, above all, aluminum chloride.

To achieve total conversion, the Friedel-Crafts catalyst is usually employed in an amount of from 1 to 1.5 moles, preferably from 1.1 to 1.2 moles, per equivalent of carboxylic halide, or in an amount of from 2 to 2.5 moles, preferably from 2.1 to 2.2 moles, per equivalent of carboxylic anhydride. Larger amounts are possible but do not usually enhance the results.

The reaction can be carried out in the absence, but preferably in the presence, of a solvent. Examples of suitable solvents are the water-insoluble aprotic solvents normally used in Friedel-Crafts reactions, for example chlorobenzene, dichlorobenzene, 1,2- dichloroethane, carbon disulfide, nitromethane, and nitrobenzene. The amount of solvent used is not critical but generally ranges from 100 to 1,000 g per mole of alkyl aromatic hydrocarbon. Larger quantities are possible but normally no further advantage is gained thereby.

The acylation takes place in the usual manner. The starting materials are reacted at a temperature of from −20° to 100° C. and preferably from 0° to 60° C. and at reduced, elevated or, preferably, standard pressure. Normally, the acylating agent is initially present in the solvent, to which the Friedel-Crafts catalyst and the alkyl aromatic hydrocarbon containing the aluminum oxane are added.

The method of working up the reaction mixture has no special features and is carried out in conventional manner by pouring the mixture into a volume of water or on to ice and isolating the acylated product from the organic phase.

In principle, all alkylated isocyclic or heterocyclic aromatic hydrocarbons can be used as starting materials, for example alkyl-substituted benzenes, naphthalenes, anthracenes, furans, benzofurans, and thiophenes. The alkyl radicals are for example those having from 1 to 20, preferably from 1 to 12 and more preferably from 1 to 8, carbon atoms. Both the alkyl radical and the aromatic ring may contain other substituents such as $C_1$-$C_4$-alkyl groups, $C_1$-$C_4$-alkoxy groups, halogen atoms such as chlorine or bromine atoms, and hydroxy groups. The aliphatic radicals may contain double or triple bonds. We particularly prefer to use alkyl benzenes having 1 or 2 branched-chain alkyl radicals.

Examples of suitable compounds are:

Toluene, ethyl benzene, n-propyl benzene, n-butyl benzene, n-pentyl benzene, n-hexyl benzene, and n-octyl benzene, and in particular isopropyl benzene, s-butyl benzene, t-butyl benzene, 2-methylbutyl benzene, 3-methylbutyl benzene, 1-methylbutyl benzene, 1,1-dimethylpropyl benzene, 1,1-dimethylbutyl benzene, 1-methylpentyl benzene, 1-ethyl-1-methylbutyl benzene, 1-ethylhexyl benzene, 1,2-dimethyl benzene, 1,4-diethyl benzene, and preferably, t-amyl benzene.

As far as we have observed, the process of the invention has no limitations with regard to the acylating agent. Suitable agents are, therefore, the fluorides and in particular, the bromides and chlorides of aliphatic, cycloaliphatic and, in particular, aromatic carboxylic acids. Examples of suitable compounds are derivatives of aromatic carboxylic acids, such as benzoyl chloride, benzoyl anhydride, and more particularly, phthalic anhydride, alkylated aromatic carboxylic acid derivatives, such as p-methylbenzoyl chloride and p-tert.-butylbenzoyl chloride, alkoxylated carboxylic acid derivatives, such as 3-methoxybenzoyl chloride and 3-phenoxybenzoyl chloride, halogenated aromatic carboxylic acid derivatives, such as o-chlorobenzoyl chloride and 2,6-dichlorobenzoyl chloride and p-nitrobenzoyl chloride, araliphatic carboxylic acid derivatives such as phenylacetic chloride and 4-chloroacetic chloride and heterocyclic carboxylic acid derivatives, such as furan-2-carboxylic chloride and thiophene-2-carboxylic chloride.

The process of the invention is particularly important for the synthesis of 4-(2′carboxybenzoyl)-t-amyl benzene from t-amyl benzene and phthalic anhydride, which product can be converted to the important compound 2-t-amyl anthraquinone, which can in turn serve as an oxygen transfer agent in the synthesis of hydrogen peroxide by the Riedl-Pfleiderer method.

EXAMPLE

To a solution of 74 g (0.5 mole) of phthalic anhydride and 200 ml of o-dichlorobenzene there were added 128 g (1 05 moles) of aluminum trichloride at a temperature of from 15° to 20° C., in small portions after which 74 g (0.5 mole) of t-amyl benzene and 27 g of the methylalumoxane

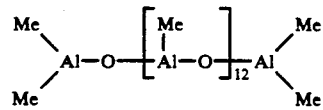

(corresponding to 0.5 mole of alkylaluminum compound) were added, and stirring was continued for 2 hours at room temperature.

The reaction mixture was worked up in conventional manner to give 4-(2′-carboxybenzoyl)-t-amyl benzene in a yield of 90%.

The same results were obtained when using the corresponding ethylalumoxane in the same molar amount.

We claim:

1. In a process for the acylation of an alkyl substituted aromatic hydrocarbon with an aromatic or aliphatic carboxylic acid halide or anhydride by the Friedel-Crafts method in the presence of a Friedel-Crafts catalyst and an organo-aluminum compound at a temperature of from −20° to 100° C., the improvement which comprises using an alumoxane as the organo-aluminum compound.

2. A process as claimed in claim 1, wherein the alumoxane used is a compound of the formula I

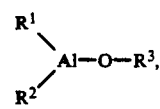

in which
$R^1$ denotes a $C_1$–$C_{12}$-alkyl group,
$R^2$ denotes a $C_1$–$C_{12}$-alkyl or $C_1$–$C_{12}$-alkoxy group, and
$R^3$ has the meaning stated for $R^1$ or denotes a radical of the formula Ia

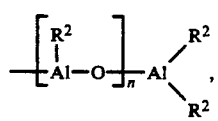

in which n has a value from 0 to 50.

3. A process as claimed in claim 1, wherein the amount of the alumoxane used is the equivalent of from 0.1 to 1.1 moles of alkyl-aluminum bonds per mole of carboxylic derivative.

4. A process as claimed in claim 1, wherein the Friedel-Crafts catalyst used is aluminum chloride or aluminum bromide.

5. A process as claimed in claim 1 wherein t-amyl benzene is acylated with phthalic anhydride.

6. A process as claimed in claim 1, wherein the alumoxane used is a compound of the formula Ib

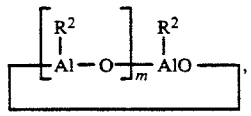
Ib in which m is a mean value ranging from 3 to 12 and $R^2$ denotes a $C_1$–$C_{12}$-alkyl or $C_1$–$C_{12}$-alkoxy group, with the proviso that the amount of the alumoxane Ib used is the equivalent of from 0.1 to 1.1 moles of alkyl aluminum bonds per mole of carboxylic derivative.

7. A process as claimed in claim 1, wherein the alumoxane used is a methylalumoxane.

8. A process as claimed in claim 2, wherein $R^1$ is $C_1$–$C_4$-alkyl and $R^2$ is $C_1$–$C_4$-alkyl or $C_1$–$C_4$-alkoxy.

9. A process as claimed in claim 6, wherein $R^2$ is $C_1$–$C_4$-alkyl or $C_1$–$C_4$-alkoxy.

10. A process as claimed in claim 1, wherein the Friedel-Crafts catalyst is used in an amount of from 1 to 1.5 moles per equivalent of carboxylic halide, as the carboxylic reactant, or in an amount of from 2 to 2.5 moles per equivalent of carboxylic anhydride, as the carboxylic reactant.

11. A process as claimed in claim 1, wherein the Friedel-Crafts catalyst is used in an amount of from 1.1 to 1.2 moles per equivalent of carboxylic halide, as the carboxylic reactant, or in an amount of from 2.1 to 2.2 moles per equivalent of carboxylic anhydride, as the carboxylic reactant.

* * * * *